United States Patent [19]
Bello et al.

[11] Patent Number: 5,505,958
[45] Date of Patent: Apr. 9, 1996

[54] TRANSDERMAL DRUG DELIVERY DEVICE AND METHOD FOR ITS MANUFACTURE

[75] Inventors: Gastone P. Bello, Monmouth Beach; John W. Lyle, Belmar; Donald A. Johnson, Sea Girt, all of N.J.

[73] Assignee: Algos Pharmaceutical Corporation, Neptune, N.J.

[21] Appl. No.: 331,724

[22] Filed: Oct. 31, 1994

[51] Int. Cl.⁶ .................................................. A61F 13/02
[52] U.S. Cl. ...................... 424/449; 424/443; 424/448; 602/46; 602/64
[58] Field of Search .................................. 424/448, 449, 424/443; 602/64, 46

[56] References Cited

U.S. PATENT DOCUMENTS

| | | | |
|---|---|---|---|
| 3,797,494 | 3/1974 | Zaffaroni | 424/434 |
| 3,814,095 | 6/1974 | Lubens | 604/307 |
| 3,996,934 | 12/1976 | Zaffaroni | 424/434 |
| 4,060,084 | 11/1977 | chandrasekaran et al. | 424/448 |
| 4,286,592 | 9/1981 | Chandrasekaran et al. | 424/448 |
| 4,379,454 | 4/1983 | Campbell et al. | 424/448 |
| 4,568,343 | 2/1986 | Leeper et al. | 424/449 |
| 4,573,995 | 3/1986 | Chen et al. | 424/449 |
| 4,588,400 | 5/1986 | Ring et al. | 604/304 |
| 4,615,699 | 10/1986 | Gale et al. | 424/448 |
| 4,733,659 | 3/1988 | Edenbaum et al. | 602/54 |
| 4,753,231 | 6/1988 | Lang | 128/156 |
| 4,764,379 | 8/1988 | Sanders et al. | 424/449 |
| 4,863,738 | 9/1989 | Taskovich | 424/449 |
| 5,006,342 | 4/1991 | Cleary et al. | 424/445 |
| 5,066,494 | 11/1991 | Becher | 424/448 |
| 5,120,300 | 6/1992 | Shaw | 602/61 |

Primary Examiner—D. Gabrielle Phelan
Attorney, Agent, or Firm—Dilworth & Barrese

[57] ABSTRACT

A transdermal drug delivery device possessing a drug-storing matrix and at least one drug delivery device-securing component is manufactured from the same flexible cellular thermoplastic resin workpiece.

19 Claims, 5 Drawing Sheets

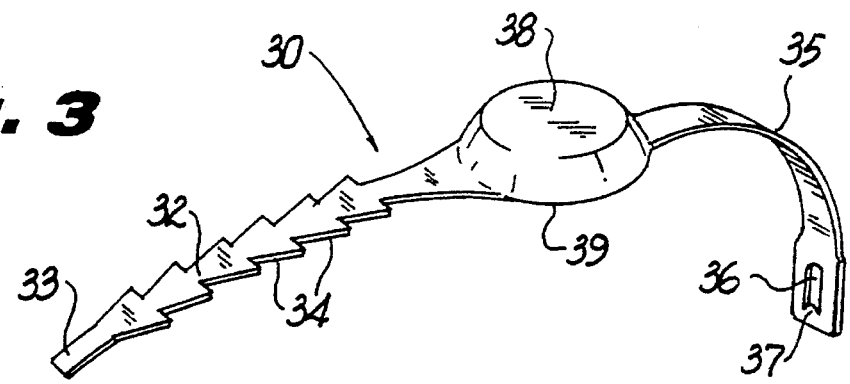
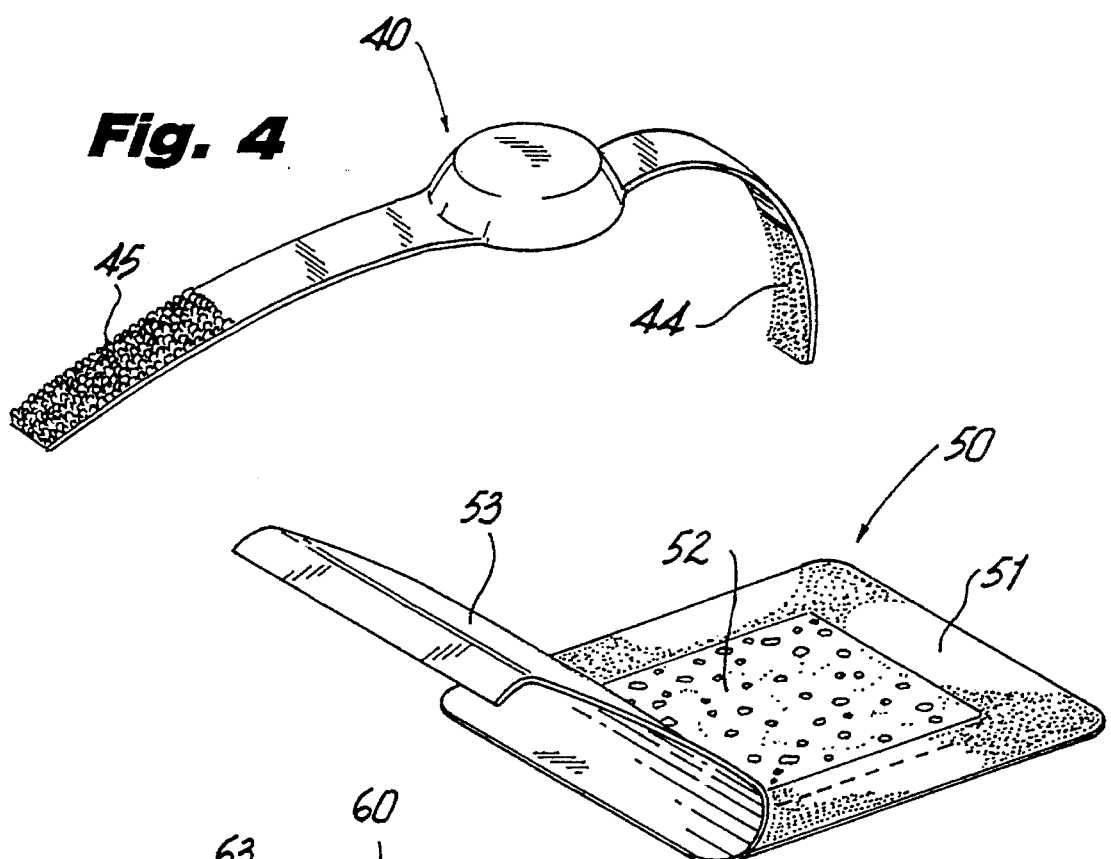
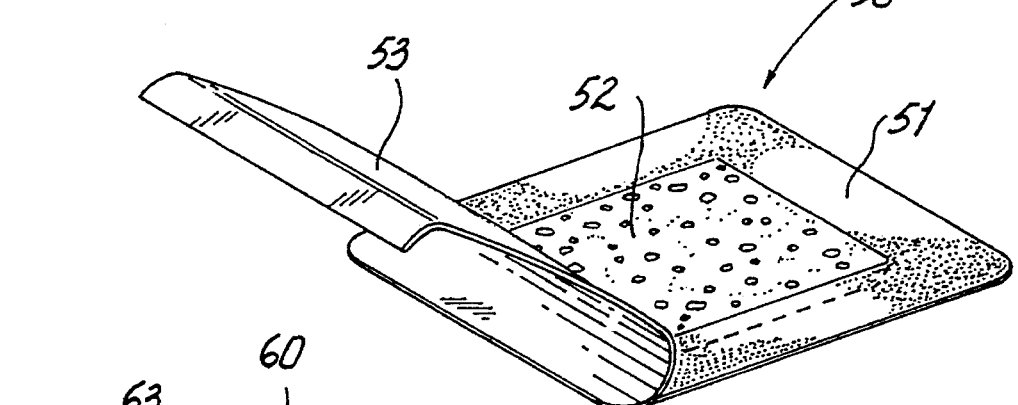
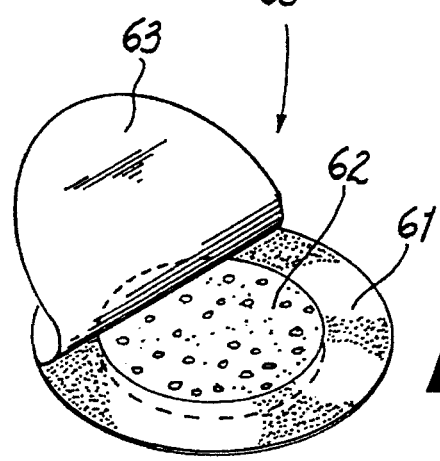

TRANSDERMAL DRUG DELIVERY DEVICE AND METHOD FOR ITS MANUFACTURE

BACKGROUND OF THE INVENTION

This invention relates to a transdermal drug delivery device and to a method for its manufacture.

A common type of transdermal drug delivery device, also variously referred to as a medical bandage, treatment pad, drug patch, etc., includes a drug reservoir or depot in the form of a drug-storing matrix or carrier and means for attaching or securing the device to a surface of unbroken skin. Representative transdermal delivery devices are described in, among others, U.S. Pat. Nos. 3,797,494; 3,996,934; 4,060,084; 4,286,592; 4,379,454; 4,568,343; 4,588,400; 4,573,995; 4,615,599; 4,764,379; 4,863,738; 5,006,342; and, 5,066,494.

SUMMARY OF THE INVENTION

In accordance with the present invention, a transdermal drug delivery device is provided which comprises:

a) a drug-storing matrix of flexible cellular structure fabricated from a flexible cellular thermoplastic resin workpiece;

b) at least one drug stored in the drug-storing matrix; and, c) at least one drug delivery device-securing component adjacent the drug-storing matrix, the drug delivery device-securing component possessing (i) a flexible component of collapsed cellular structure resistant to penetration of drug from the drug-storing matrix and fabricated from the same thermoplastic resin workpiece as the latter, the component of collapsed cellular structure together with the drug-storing matrix constituting a seamless unitary whole and (ii) means attached to, or defined on, the component of collapsed cellular structure for securing the drug delivery device to a surface of unbroken skin.

Further in accordance with this invention, a transdermal drug delivery device possessing a drug-storing matrix having at least one drug stored therein and at least one drug delivery device-securing component is manufactured by the method which comprises:

a) designating a first region of a flexible cellular thermoplastic workpiece as a region in which the cellular structure of the workpiece is to be irreversibly collapsed and a second region of the workpiece as a region in which a drug-storing cellular structure is to be retained;

b) irreversibly collapsing the cellular structure in the first region of the workpiece prior to or following storing at least one drug in the second region of the workpiece, the second region of drug-storing cellular structure providing the drug-storing matrix of the drug delivery device, the first region of collapsed cellular structure and the second region of drug-storing cellular structure constituting a seamless unitary whole; and, c) providing the first region of collapsed cellular structure with means for securing the drug delivery device to a surface of unbroken skin, the first region of collapsed cellular structure and the means for securing the drug delivery device providing the drug delivery device-securing component of the drug delivery device.

The foregoing transdermal drug delivery device is of simpler construction than known drug delivery devices which feature a drug-storing matrix or carrier. In addition, the method of manufacturing the drug delivery device of this invention offers technical and economical advantages over the manufacturing procedures for making such known devices. Thus, the device of this invention employs a single material, namely, a flexible, cellular thermoplastic resin, as the workpiece from which the drug-storing matrix and all, or nearly all, of the drug delivery device-securing component are manufactured. This enables the transdermal drug delivery device herein to be manufactured at a significantly lower unit cost than known devices which also include a drug-diffusing matrix or carrier.

As used herein, the term "transdermal" applies not only to transdermal drug delivery as such but to topical and/or percutaneous delivery of drug as well.

BRIEF DESCRIPTION OF THE DRAWINGS

FIG. 3 illustrates in plan view another transdermal drug delivery device in accordance with this invention, adapted for encircling a body part, in which the drug delivery device-securing component possesses locking means for securing the device to a body surface;

FIG. 4 illustrates in side elevation view a transdermal drug delivery device in accordance with this invention, also adapted for encircling a body part, wherein the drug delivery device-securing component possesses hook and loop elements for securing the device to a body surface;

FIGS. 5 and 6 illustrate in perspective view embodiments of the transdermal drug delivery device of this invention in which the drug delivery device-securing component is provided as a continuous region surrounding the drug-storing matrix;

DESCRIPTION OF THE PREFERRED EMBODIMENTS

Figure 1:
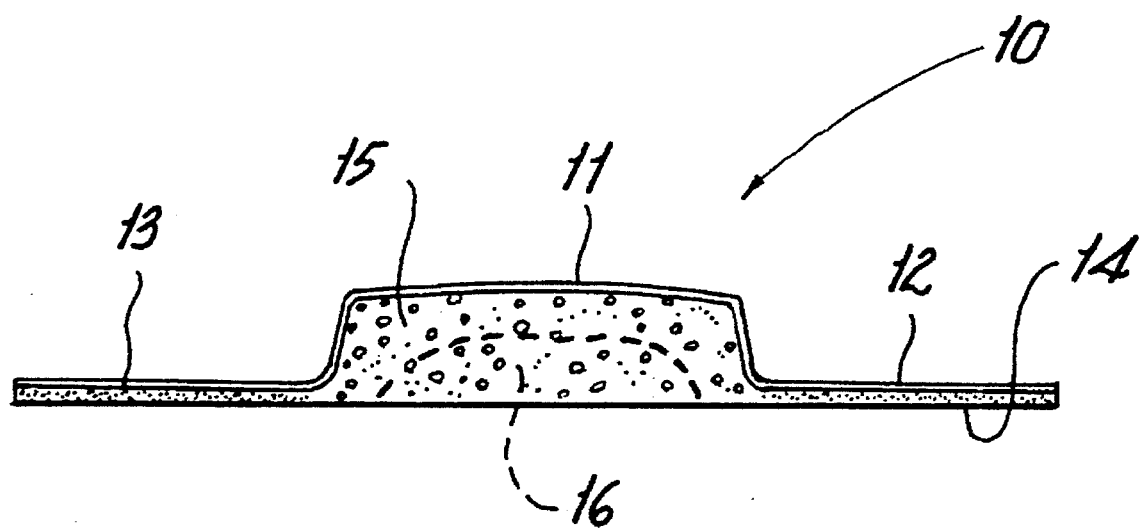
FIGS. 1 and 2 illustrate in side elevation view two embodiments of a transdermal drug delivery device in accordance with this invention.

One embodiment of a transdermal drug delivery device in accordance with this invention is shown generally in FIG. 1 at 10. The drug delivery device features an optional flexible, drug-impermeable film or coating 11 to prevent diffusion of drug to an exterior upper surface of the device. If desired, optional film or coating 11 can be confined to just the upper surface of flexible, cellular drug-storing, drug-releasing matrix 15 since this is the portion of the dressing that would principally benefit from the barrier properties of a drug-impermeable film or coating. Drug delivery device 10 is secured to an unbroken surface of skin by first and second straps 12 and 13 coated on their skin-contacting sides with pressure-sensitive adhesive 14. Straps 13 and 14 are formed from the same flexible cellular thermoplastic resin workpiece as drug-storing matrix 15 and together with the latter, form a seamless unitary whole. Straps 12 and 13 are formed by compressing and heating certain sections of the aforementioned workpiece as a result of which such sections acquire a collapsed cellular structure which resists penetration by drug stored in drug-storing matrix 15. Since straps 12 and 13 and drug-storing matrix 15 are fabricated from the same workpiece, their flexing properties are somewhat similar. The resulting similarity of response to flexing forces which is characteristic of components 12, 13 and 15 of the drug delivery device herein enables the device to better conform to the surface of a flexing site to which the device may be applied.

A therapeutically effective amount of at least one topical or transdermal drug is incorporated into drug-storing matrix 15. Suitable drugs include topically delivered local anesthetics such as benzocaine, procaine hydrochloride, tetracaine, tetracaine hydrochloride, dibucaine, lidocaine, lidocaine hydrochloride, bupivicaine, dyclonin, etidocaine, mepivicaine, butamen picrate, dimethisoquin hydrochloride, cyclomethylcaine sulfate, and the like; analgesics and anti-inflammatory agents such as buprenorphin, butophanol tartrate, acetaminophen, fentanyl, mefenamic acid, flutenamic acid, diclofenac, oxyphenbutazone, phenybutazone, ibuprofen, flurbiprofen, naproxen, menthol, methyl salicylate, phenol, salicylic acid, benzyl alcohol, 1-menthol, camphor, camphorated metacresol, juniper tar, resorcinol, allyl isothiocyanate, capsaicin, and the like; cortico steroids such as alclometasone dipropionate, amcinocide, hydrocortisone, betamethasone dipropionate, betamethasone valerate, desoximetasone, clobetasol propionate, flurandrenolide, halcinonide, halobetasol, estradiol, testosterone, progesterone, fluticasone, clobetasol, dexamethasone, dexonide, fluocinolone acetonide, flucinonide, medroxyprogesterone, mometasone furoate, triamcinolone, and the like; antibiotics such as bacitracin, bacitracin zinc, chlortetracycline hydrochloride, chlorhexadine gluconate, clindamycin, cliquinol, neomycin sulfate, polymyxin B sulfate, erythromycin, gentamicin, sulfathiazole, sulfacetamide, sulfabenzamide, oxytetracycline hydrochloride, tetracycline, and the like; antimicrobial agents such as benzalkonium chloride, chlorhexidine gluconate, hexaclorophene, mafenide acetate, nitrofurazone, nystatin, acetosulfamine, clortrimazole, povidone-iodine, and the like; antifungal agents such as amphotericin B, butoconazole, cetylpyridinium chloride, chlorxylenol, cyclopirox olamine, clioquinol, clotrimazole, sulconazole nitrate, nystatin, oxyconazole, econazole nitrate, ketoconazole, miconazole nitrate, naftifine hydrochloride, pentamycin, pyrrolinitrin, terbinafine, triacetin, and the like; debriding agents such as deoxyribonuclease, collagenolytic, debridement, fibrinolytic or proteolytic enzymes, papain, papain-urea, and the like; antihistamines such as chlorcyclizine hydrochloride, diphenylhydramine hydrochloride, tripelennamine hydrochloride, and the like; antiepileptics such as nitrazepam, meprobamate, clonazepam, and the like; coronary vasodilators such as nitroglycerine, dipyridamole, erythritol, tetranitrate, pentaerythritol tetranitrate, propatylnitrate, and the like; and other drugs such as benzoyl peroxide, podofilox, masoprocol, nicotine, scopolamine, nitroglycerine, fluorouracil, hydrocolloids, hydroquinone, monobenzone, tretinoin and acyclovir.

These and other drugs will ordinarily be provided in some suitable diffusable medium, e.g., gel, cream, or ointment 16, in accordance with well established pharmaceutical formulating practice. In those cases where rapid penetration of the drug is desired, it is advantageous to include one or more penetration enhancers in the diffusable drug composition. Included among the penetration enhancers that can be used herein are butylene glycol, capric acid, caproic acid, caprylic acid, caprylic/capric triglyceride, diethylene glycol, diethylene glycol monoethyl ether, glycerin, glyceryl dioleate, glycerol monooleate, glycerol trioleate, hexylene glycol, isopropylmyristate, isopropylpalmitate, linoleic acid, methyl laurate, oleic acid, oleyl alcohol, polyethylene glycol 200, polyethylene glycol dilaurate, propyl oleate, propylene glycol, squalene, and the like.

Figure 2:
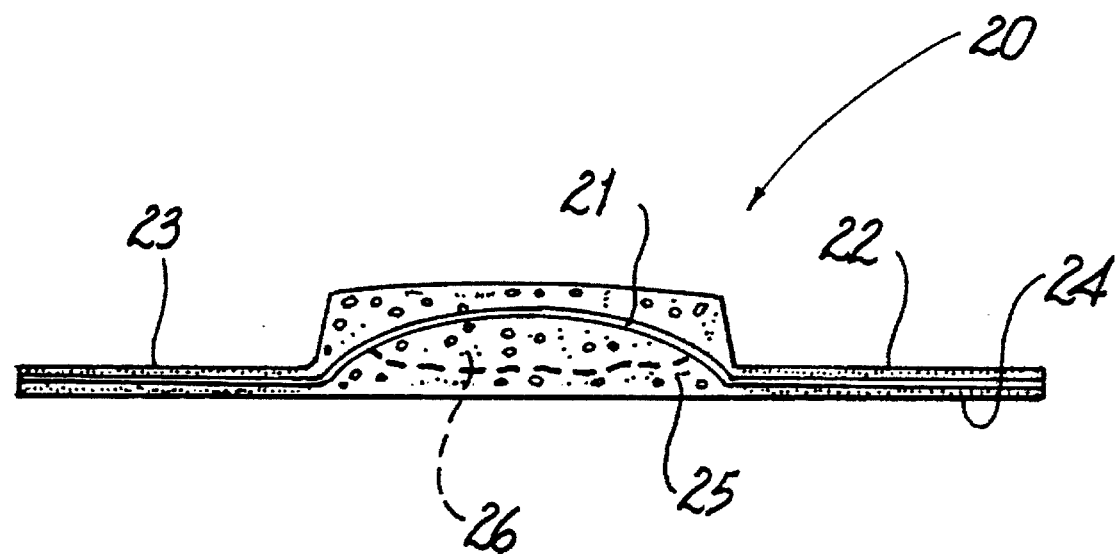

FIGS. 2–6 illustrate other embodiments of the drug delivery device of this invention. Drug delivery device 20 of FIG. 2 shows optional flexible, drug-impermeable film or layer 21 disposed within the interior structure of the device. On the skin-facing side of film or layer 21 and within drug-storing, drug-releasing matrix 25 is a region of diffusible drug composition 26. Straps 22 and 23 with their coating of adhesive 24 provide the drug delivery device-securing component as in the embodiment of FIG. 1.

FIG. 3 illustrates a drug delivery device of this invention, 30, adapted for encircling a body part. Drug-storing, drug-releasing matrix 38 is shown with its skin-contacting surface 39 in the face-down position. The drug delivery device-securing component includes first strap 32 of collapsed cellular structure having defined thereon leader 33 and arrowhead-like projections 34 and second strap 35 of collapsed cellular structure possessing aperture 36 and retainer flap 37. The configurations of straps 32 and 35 can be conveniently formed by a die-cutting operation. Leader 33 of strap 32 when inserted in aperture 36 of strap 35 and drawn back in a tightening action results in strap 32 being locked in place by retainer flap 37.

As shown in FIG. 4, another embodiment of a body part-encircling drug delivery device in accordance with this invention, drug delivery device 40 possesses, as the drug delivery device-securing component, first strap 42 the interior side of which is bonded to pad 44 covered with numerous woven filaments formed into permanent hooks and second strap 43 the exterior side of which is bonded to pad 45 covered with numerous soft loops. When pressed together, straps 42 and 43 form a shear-resistant band which can, however, be separated by simply being pulled apart.

In drug delivery device 50 of FIG. 5, securing component 51 of the device is provided as a continuous band of pressure-sensitive adhesive-coated material of collapsed cell structure surrounding drug-storing, drug-releasing matrix 52 (shown in the inverted position). Peelable film 53 covers the skin-contacting surface of the drug delivery device until the latter is ready to be used. Drug delivery device 60 of FIG. 6 is similar to that of FIG. 5 except for having a circular configuration. Otherwise, components 61, 62 and 63 correspond to components 51, 52 and 53 of the embodiment shown in FIG. 5.

Figure 7:
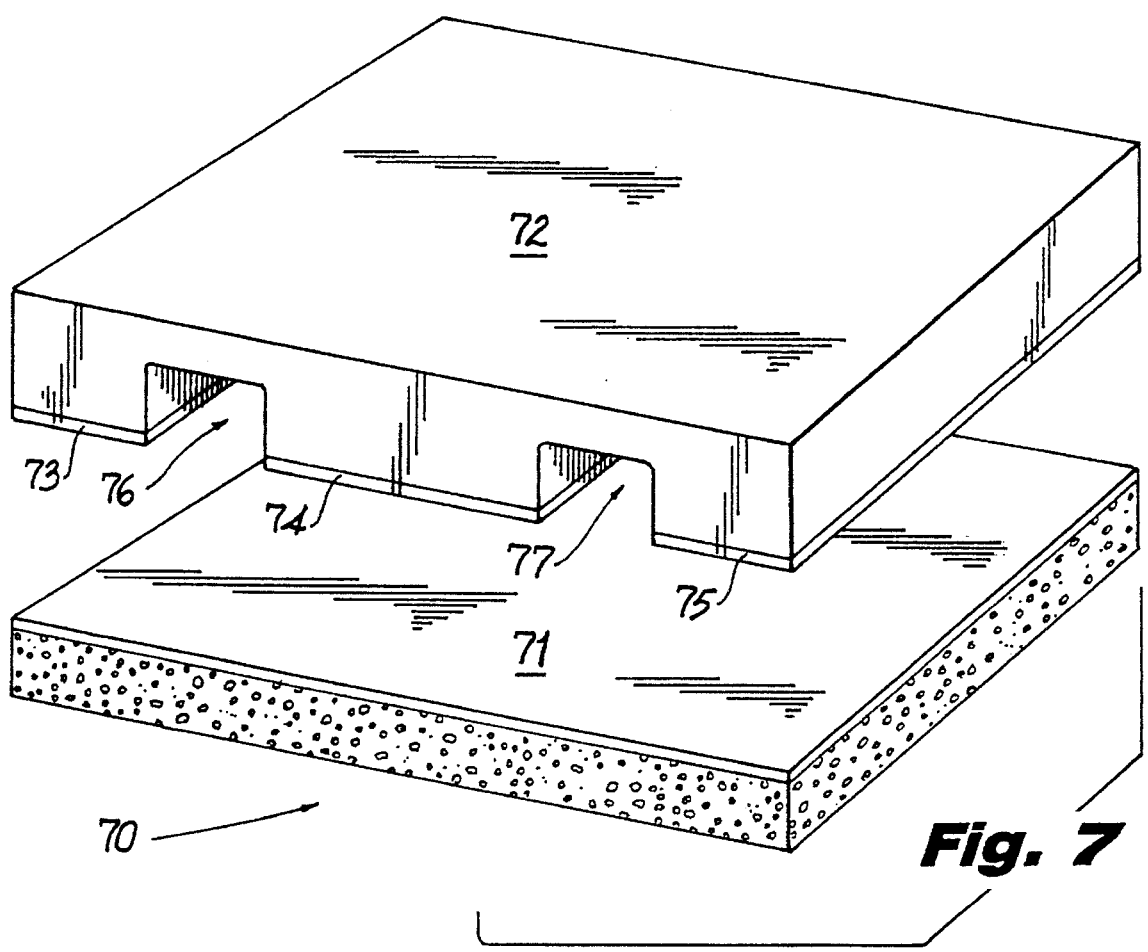
FIGS. 7 and 8 illustrate a method for manufacturing the transdermal drug delivery device of FIG. 1; and, FIGS. 9–14 illustrate a method for manufacturing the transdermal drug delivery device of FIG. 2.
Figure 8:
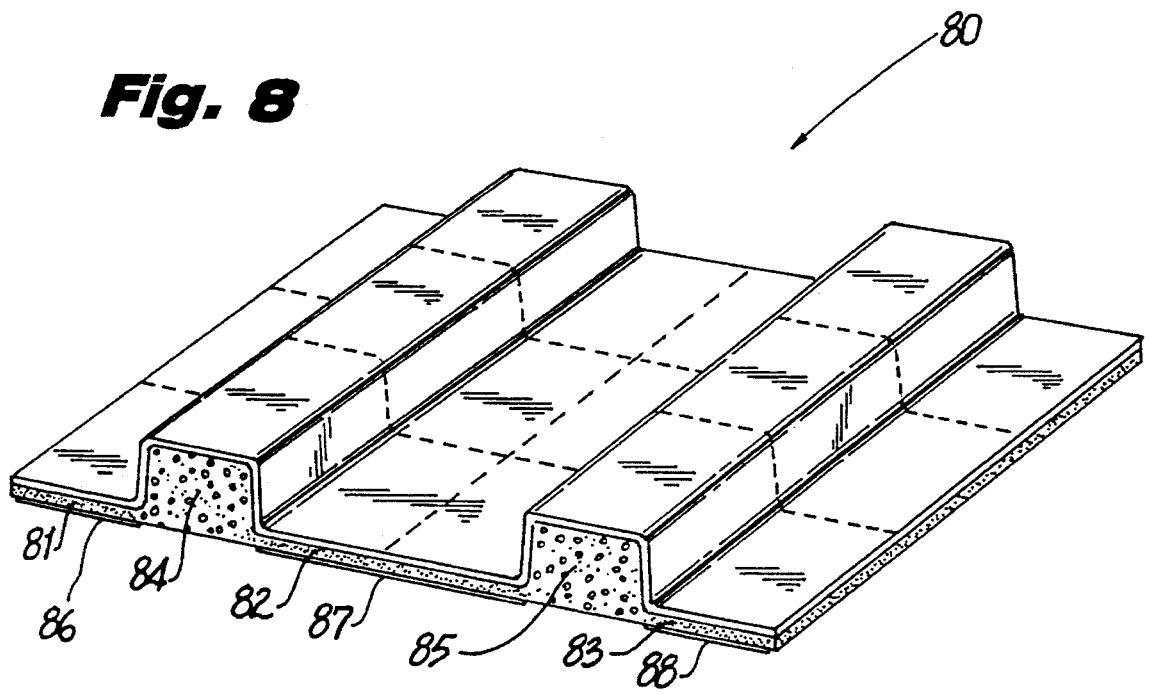

FIGS. 7 and 8 schematically illustrate a method of manufacturing drug delivery device 10 of FIG. 1. Workpiece 70 is fabricated from a flexible cellular (i.e., foamed) thermoplastic resin. The characteristics of workpiece 70 can vary considerably. For example, the workpiece can have a thickness of from about $\frac{1}{16}$ to about 2 in., a void volume of up to about 98 percent, an average cell size of from about 200 to about 2,000 microns and a density of from about 1.3 to about 10 lb/ft$^3$. Among the cellular thermoplastic resins that can be used as workpiece 70 are polyurethanes, latex foam rubbers, poly(vinyl chloride) resins, silicone resins, and the like. For details regarding a particular cellular resin, see, e.g., standard reference works such as the "*Encyclopedia of Polymer Science and Technology*", Mark et al. eds., 2nd ed., Vol. 3, pp. 6–14 (Wiley, 1985). The cell structure of workpiece 70 can be reticulated or non-reticulated and is advantageously of the open cell type to achieve good levels of drug retention and diffusion. Filtercrest® and Feltcrest® reticulated polyurethane foams available from Crest Foam Industries, Inc., 100 Carol Place, Moonachie, NJ 07074 are suitable for use as workpiece 70. Other suitable polyurethane foams include those disclosed in U.S. Pat. Nos. 3,975,567, 3,978,855, 4,960,594, 5,154,928 and 5,164,421, the contents of which are incorporated by reference herein.

Drug delivery device 10 can possess a drug-impermeable film or layer 71 as an optional component when barrier properties are desired. Optional drug-impermeable component 71 can be provided as a thermoplastic film, e.g., a polyethylene film of from about 0.005 to about 0.01 cm thickness bonded to the upper surface of workpiece 70, or as a layer of material which imparts drug barrier properties to the upper surface of the workpiece, e.g., a coating of molten polyethylene resin which on application to said surface infiltrates the uppermost zone of cells and on solidification provides a drug-impermeable stratum to a depth of from about 0.01 to about 0.1 cm. As a matter of manufacturing convenience, drug-impermeable component 71 can be applied to the entire upper surface of workpiece 70; however, where barrier properties are desired, drug-impermeable component 71 can be confined to just those areas of the upper surface of workpiece 70 in cellular regions 84 and 85 (FIG. 8). As an alternative to the aforedescribed procedure of applying optional drug-impermeable component 71 to workpiece 70, this component can be applied to the reshaped workpiece of FIG. 8. So-called integral skin foams can be used as workpiece 70; such foams possess a relatively dense drug-impermeable skin surface and a drug-storing, drug-releasing cellular core. Splitting an integral skin foam into two layers provides two workpieces each of which possesses a drug-impermeable surface and a drug-storing, drug-releasing interior. Such workpieces dispense with the need to add a separate drug-impermeable component when barrier properties are desired.

Workpiece 70 is selectively and permanently reshaped in certain limited and defined regions thereof to provide reshaped workpiece 80 of FIG. 8. These regions of workpiece 70 individually and collectively constitute a first region of the workpiece. The remaining regions of workpiece 70 which are to retain a drug-storing, drug-releasing cellular structure individually and collectively constitute a second region of the workpiece. If desired, a quantity of drug may be incorporated into the second region of workpiece 70 prior to the reshaping operation or such incorporation may be accomplished after the reshaping operation. One suitable means for accomplishing the reshaping of the first region of workpiece 70 is shown in FIG. 7 and utilizes a platen 72 having electrically heated elements 73, 74 and 75, optionally provided with a release coating, which correspond to collapsed cellular regions 81, 82 and 83 of reshaped workpiece 80 of FIG. 8 and channels 76 and 77 which correspond to retained cellular regions 84 and 0 85 of reshaped workpiece 80. When heated elements 73, 74 and 75 are applied under pressure against the first region of workpiece 70, they produce the configuration of reshaped workpiece 80. Thus, heated elements 73, 74 and 75 compressively applied to the first region of workpiece 70 result in an irreversible collapse of the cell structure in this region the result being that the region resists penetration by diffusable drug compared to the unaffected second region of the workpiece, i.e., non-heated, non-compressed cellular regions 84 and 85 of reshaped workpiece 80 which retain their ability to store and release drug. In place of platen 72, any other means for applying heat and pressure to preselected areas of workpiece 70 can be used, e.g., heated rolls. As another alternative, pairs of platens or rolls applied to the upper and lower sides of workpiece 70 can also be used to achieve the requisite reshaping of the workpiece. It is, of course, within the scope of this invention to partially collapse part or all of the second region of workpiece 70 provided, of course, the resulting partially collapsed cellular regions retain significant capability for storing and releasing drug.

The cellular regions of workpiece 70 which are to be collapsed must be heated to a temperature which is at or near the softening point of the foam. This temperature will, of course, depend on the nature of the foam. The temperature of heated elements 73, 74 and 75 can be from about 100° to about 250° C. and preferably is from about 110° to about 200° C. for many of the cellular thermoplastic resins from which workpiece 70 can be fabricated. Similarly, the amount of pressure applied to the aforementioned regions of workpiece 70 will depend on the nature of the foam. This pressure can range from slightly above atmospheric to up to about 500 p.s.i. and is preferably from about 50 to about 120 p.s.i. In any event, the conditions of temperature and pressure must be such as to provide collapsed cell regions 81, 82 and 83 (FIG. 8) that resist taking up drug that has, or will have, been incorporated in cellular regions 84 and 85 when these regions assume their roles as the drug-storing matrices of individual drug delivery devices. Cell collapse need not be complete to achieve a satisfactory degree of such resistance. For example, the application of heat and pressure sufficient to reduce the thickness of workpiece 70 by 80 to 95 percent in the affected regions (i.e., 81, 82 and 83 of reshaped workpiece 80) will usually provide a suitable level of resistance to penetration by drug.

Following the manufacturing operation which provides reshaped workpiece 80, the skin-contacting side of collapsed cell regions 81, 82 and 83 are provided with coatings 86, 87 and 88 of pressure-sensitive adhesive numerous kinds of which are known in the art. Before or after application of the adhesive and if not previously accomplished, a desired quantity of drug, usually in a carrier providing a diffusible medium, is incorporated in cellular regions 84 and 85. The adhesively coated side of reshaped workpiece 80 can, if desired, be provided with a peelable release sheet. Finally, reshaped workpiece 80 is cut along dotted lines 89a and 89b to provide individual drug delivery devices 10 as shown in FIG. 1 (six in FIG. 8 but many more in a commercial manufacturing method) which are thereafter packaged and sterilized employing known and conventional techniques.

FIGS. 9–14 schematically illustrate a method for manufacturing the drug delivery device of FIG. 2 and shares much in common with the manufacturing method of FIGS. 7 and 8 which was just described.

Figure 9:
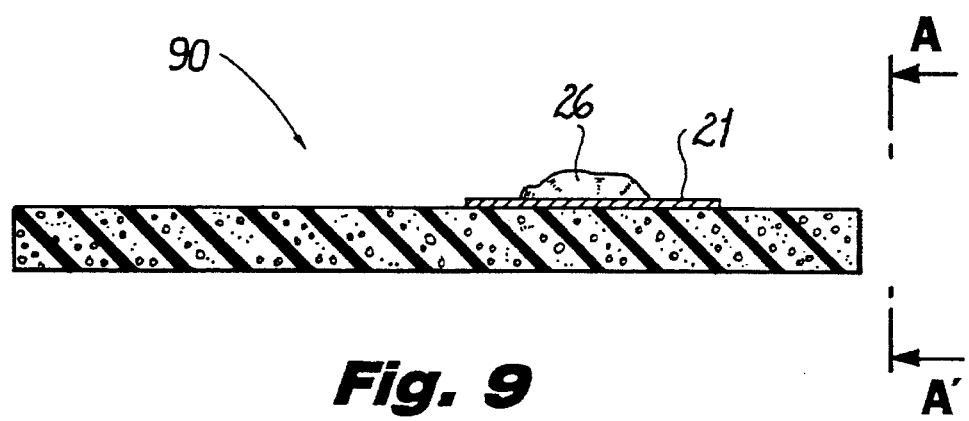
Figure 10:
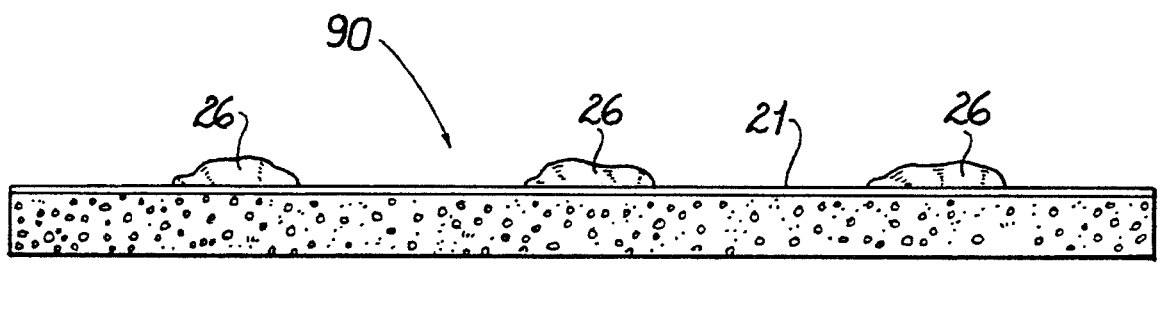
Figure 11:
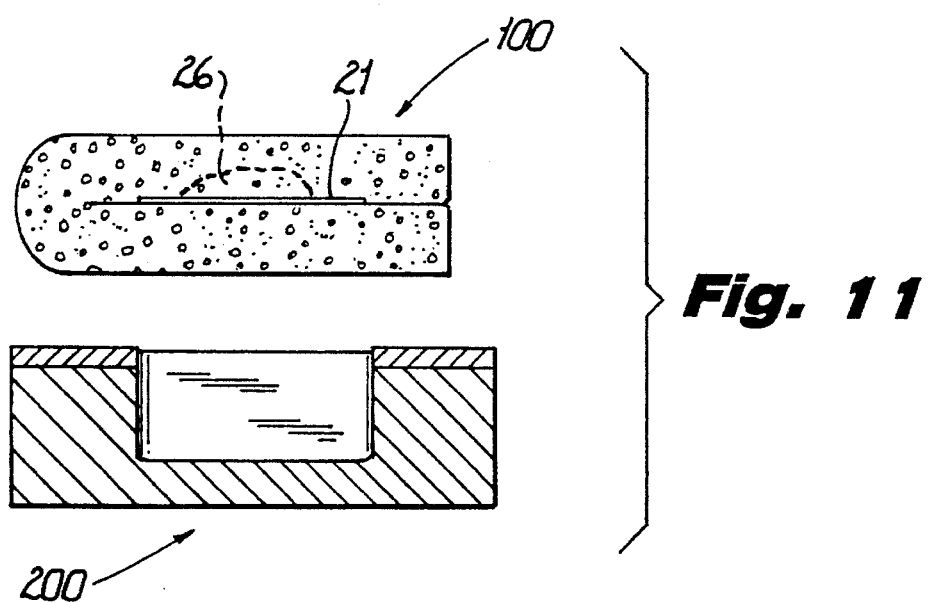
Figure 12:
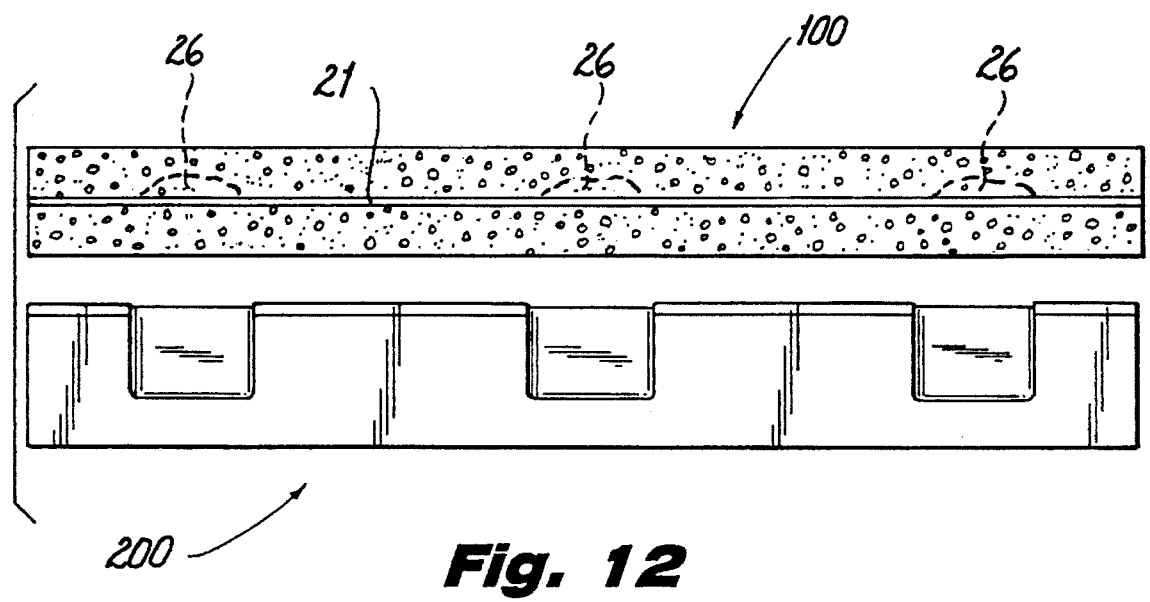
Figure 13:
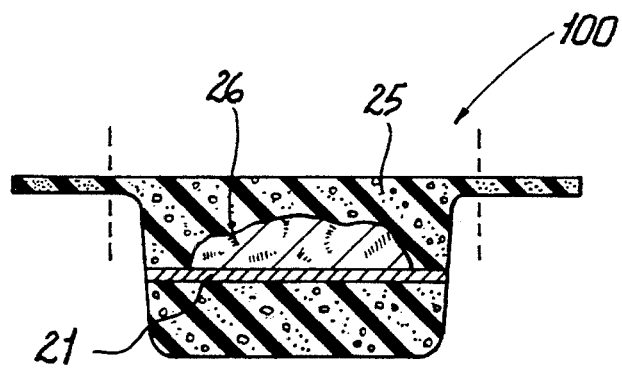
Figure 14:
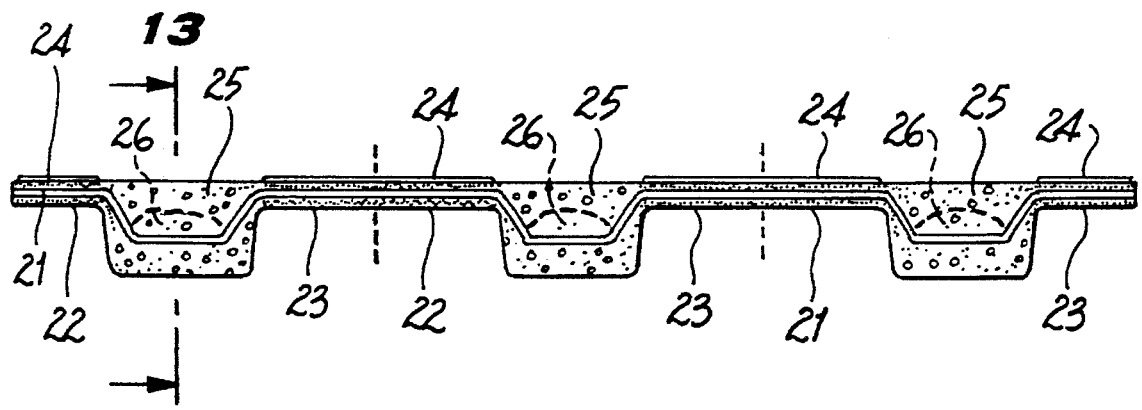

As shown in FIG. 9, a cross-sectional view of flexible cellular workpiece 90, drug-impermeable film or layer 31 is positioned at one upper side of the workpiece with a quantity of drug 26 formulated as a gel, cream or ointment deposited upon film or layer 21. FIG. 10 shows these same elements in side elevation taken along line A—A' of FIG. 9. In FIGS. 11 and 12, respectively, cross-sectional and side elevation views of workpiece 100 folded over lengthwise to provide a workpiece assembly, platen 200 with its heated elements is positioned relative to the assembly as shown. Of course, instead of folding workpiece 100 over to sandwich film or layer 21 between the folds of cellular material, two workpieces can be used with one placed above the other to provide an equivalent assembly. The principle of operation of platen 200 is identical to that of platen 72 of FIG. 7. As a result of application of heated platen 200 to the workpiece assembly under pressure, the latter is reshaped as shown in the cross-sectional and side elevation views of FIGS. 13 and 14. The dotted lines in FIG. 13 indicate cut lines where excess collapsed cell material can be removed if desired. As shown in FIG. 14, dotted lines indicate where collapsed cell regions 22 and 23 can be cut to provide individual drug delivery devices 20 as shown in FIG. 2.

Although several embodiments of the wound dressing and method for manufacturing a wound dressing in accordance with the present invention have been described in detail, it is understood that obvious variations can be made without departing from the spirit and scope of the invention as defined by the appended claims.

What is claimed is:

1. A transdermal drug delivery device which comprises:
   a) a drug-storing matrix of flexible cellular structure fabricated from a flexible cellular thermoplastic resin workpiece;
   b) at least one drug stored in the drug-storing matrix; and,
   c) at least one drug delivery device-securing component adjacent the drug-storing matrix for securing the drug delivery device to a surface of unbroken skin, the drug delivery device-securing component possessing a flexible component of collapsed cellular structure resistant to penetration of drug from the drug-storing matrix and fabricated from the same thermoplastic resin workpiece as the drug-storing matrix, the drug delivery device-securing component together with the drug-storing matrix constituting a seamless unitary whole.

2. The drug delivery device of claim 1 wherein the drug-storing matrix possesses a drug-impermeable barrier film or layer to prevent diffusion of drug to an exterior surface of the drug delivery device.

3. The drug delivery device of claim 1 wherein the drug delivery device-securing component includes first and second strap members of collapsed cell structure extending from opposite sides of the drug-storing matrix.

4. The drug delivery device of claim 1 wherein the drug delivery device-securing component includes a continuous band of collapsed cell structure surrounding the drug-storing matrix, the band of collapsed cell structure being coated with pressure-sensitive adhesive on the skin-contacting side thereof.

5. The drug delivery device of claim 3 wherein the first and second strap members are coated with pressure-sensitive adhesive on the skin-contacting sides thereof.

6. The drug delivery device of claim 3 adapted for encircling a body part wherein the first strap member possesses arrowhead projections and the second strap member possesses an aperture and retaining tab for locking engagement with the arrowhead projections of the first strap member.

7. The drug delivery device of claim 3 adapted for encircling a body part wherein the first strap member is provided with hooks and the second strap member is provided with loops, the hooks of the first strap member being engageable with the loops of the second strap member to form a shear-resistant band.

8. The drug delivery device of claim 2 wherein the drug-impermeable barrier film or layer is disposed within the interior of the drug-storing matrix.

9. The drug delivery device of claim 1 wherein the skin-contacting surface of the drug delivery device-securing component and the skin-contacting surface of the drug-storing matrix lie substantially in the same plane.

10. The drug delivery device of claim 1 wherein the drug-storing matrix and the component of collapsed cellular structure are formed from a polyurethane resin workpiece.

11. The drug delivery device of claim 1 wherein the drug is a local anesthetic.

12. The drug delivery device of claim 11 wherein the local anesthetic is combined with a penetration enhancer.

13. The drug delivery device of claim 1 wherein the drug is an antibiotic.

14. A method for manufacturing a transdermal drug delivery device possessing a drug-storing matrix having at least one drug stored therein and at least one drug delivery device-securing component, which comprises:
   a) designating a first region of a flexible cellular thermoplastic workpiece as a region in which the cellular structure of the workpiece is to be irreversibly collapsed and a second region of the workpiece as a region in which a drug-storing cellular structure is to be retained;
   b) irreversibly collapsing the cellular structure in the first region of the workpiece prior to or following storing at least one drug in the second region of the workpiece, the second region of drug-storing cellular structure providing the drug-storing matrix of the drug delivery device, the first region of collapsed cellular structure and the second region of drug-storing cellular structure constituting a seamless unitary whole; and,
   c) providing the first region of collapsed cellular structure with means for securing the drug delivery device to a surface of unbroken skin, the first region of collapsed cellular structure and the means for securing the drug delivery device providing the drug delivery device-securing component of the drug delivery device.

15. The method of claim 14 wherein heat and pressure are applied to the first region of the workpiece to irreversibly collapse the cellular structure of the workpiece in such region.

16. The method of claim 14 wherein the drug-storing matrix is provided with a drug-impermeable barrier to present diffusion of drug to an exterior surface of the drug delivery device.

17. The method of claim 16 wherein the drug-impermeable barrier is interposed between layers of workpiece to provide a workpiece assembly and heat and pressure are applied to the first region of the workpiece assembly to irreversibly collapse the cellular structure in such region and bond the layers of workpiece and drug-impermeable barrier to each other in such region.

18. The method of claim 14 wherein the skin-contacting surface of the first region of collapsed cellular structure and the skin-contacting surface of the second region of drug-diffusing cellular structure lie substantially in the same plane.

19. The method of claim 14 wherein the workpiece is a thermoplastic polyurethane resin workpiece.

* * * * *